US00PP32456P2

(12) United States Plant Patent
Radler

(10) Patent No.: US PP32,456 P2
(45) Date of Patent: Nov. 17, 2020

(54) GRANDIFLORA ROSE PLANT NAMED 'RADBEAUTY'

(50) Latin Name: *Rosa hybrida*
Varietal Denomination: Radbeauty

(71) Applicant: The Conard-Pyle Company, West Grove, PA (US)

(72) Inventor: William Radler, Greenfield, WI (US)

(73) Assignee: The Conard-Pyle Company, West Grove, PA (US)

( * ) Notice: Subject to any disclaimer, the term of this patent is extended or adjusted under 35 U.S.C. 154(b) by 0 days.

(21) Appl. No.: 16/602,931

(22) Filed: Dec. 30, 2019

(51) Int. Cl.
*A01H 5/02* (2018.01)
*A01H 6/74* (2018.01)

(52) U.S. Cl.
USPC ..... Plt./137

(58) Field of Classification Search
USPC ..... Plt./101, 130, 137
See application file for complete search history.

(56) References Cited

U.S. PATENT DOCUMENTS

PP1,259 P 2/1954 Lammerts

*Primary Examiner* — Susan McCormick Ewoldt
*Assistant Examiner* — Karen M Redden
(74) *Attorney, Agent, or Firm* — Panitch Schwarze Belisario & Nadel LLP

(57) ABSTRACT

A new and distinct variety of Grandiflora rose plant, herein referred to by its cultivar name, 'Radbeauty', is provided which forms abundantly on a substantially continuous basis attractive, cup-like shaped pink colored blossoms. Attractive semi-glossy foliage is formed, which contrasts beautifully with the blossoms. The growth habit is very bushy and rounded. The new variety is well suited for providing attractive ornamentation in the landscape.

1 Drawing Sheet

Botanical/commercial classification:
Latin name—*Rosa hybrida.*
Varietal denomination: 'Radbeauty'.

SUMMARY OF THE INVENTION

The new variety of *Rosa hybrida* Grandiflora rose plant was created during June of 2004 in Milwaukee, Wis., U.S.A., by artificial pollination wherein two parents were crossed which previously had been studied in the hope that they would contribute the desired characteristics. The female parent (i.e., the seed parent) was an unnamed breeder seedling (not patented). The male parent (i.e., the pollen parent) was a different unnamed breeder seedling (not patented).

The parentage of the new variety can be summarized as follows:

unnamed breeder seedling female parent x unnamed breeder seedling male parent

The seeds resulting from the above pollination were sown and small plants were obtained which were physically and biologically different from each other. Selective study resulted in the identification of a single plant of the new variety.

It was found that the new variety of rose plant of the present invention possesses the following combination of characteristics:

(a) forms attractive, cup-like shaped, pink colored blossoms,
(b) displays a very bushy and rounded growth habit,
(c) forms vigorous vegetation, and
(d) provides attractive ornamental dark green, semi-glossy foliage.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the unnamed breeder seedling female parent (i.e., seed parent) displays flowers with more petals, a less compact growth habit, and foliage with less glossy appearance compared to the new variety. In addition, the unnamed breeding seedling male parent (i.e., the pollen parent) displays flowers with less petals, a darker green colored foliage which has a more glossy appearance, and has less compact growth habit compared to the new variety. Moreover, the new variety can be readily distinguished from other similar non-parental varieties. For example, the 'Queen Elizabeth' variety (U.S. Plant Pat. No. 1,259) displays flowers with more petals and a more pointed bud shape.

The new variety has been found to undergo asexual propagation at Wasco, Calif. and at Cochranville, Pa. by a number of routes, including vegetative cuttings. Asexual propagation by vegetative cuttings at Wasco, Calif. and at Cochranville, Pa. has shown that the characteristics of the new variety are stable and are strictly transmissible by such asexual propagation from one generation to another. Accordingly, the new variety undergoes asexual propagation in a true-to-type manner.

The new variety has been named 'Radbeauty'.

The new variety was not sold or offered for sale as of Dec. 30, 2019.

BRIEF DESCRIPTION OF THE PHOTOGRAPH

The accompanying photograph of FIG. 1 shows as nearly true as it is reasonably possible to make the same, in a color illustration of this character, a typical specimen of the new variety. The rose plant of the new variety was approximately three years of age and was observed during May 2019 while growing on its own roots and growing outdoors at Cochranville, Pa., U.S.A.

FIG. 1—illustrates a specimen a plant with open blossoms.

DETAILED BOTANICAL DESCRIPTION

The chart used in the identification of the colors is that of The Royal Horticultural Society (R.H.S. Colour Chart, 2015 edition), London, England. The terminology which precedes reference to the chart has been added to indicate the corresponding color in more common terms. The description is based on the observation of three-year-old specimens of the new variety during August while growing on their own roots in the ground at Cochranville, Pa., U.S.A.

Commercial classification: Grandiflora Rose Plant.

Plant:

*Habit*.—Very bushy and rounded.

*Height*.—Approximately up to 3 ft on average.

*Width*.—Approximately 3.5 ft on average.

Branches:

*Color*.—Young stems: commonly near Yellow-Green Group 144A. — old wood: commonly near Yellow-Green Group 146B.

*Length*.—Main stems: approximately 60.0 cm on average. — secondary stems: approximately 20.0 cm on average.

*Diameter*.—Main stems: approximately 9.0 mm on average. — secondary stems: approximately 6.0 mm on average.

*Thorns*.—Young thorns: length is approximately 3.0 mm on average, width is approximately 3.0 mm on average at point of attachment, and color is commonly near Red-Orange Group 34B. — old thorns: length is approximately 6.0 mm on average, width is approximately 4.0 mm on average at point of attachment, and color is commonly near Greyed-Orange Group 165A.

Foliage:

*General appearance*.—Dark green with a semi-glossy aspect.

*Young foliage*.—Upper surface color: commonly near Yellow-Green Group 146A blended with near Greyed-Purple Group 183C with venation of near Greyed-Purple Group 183B. — under surface color: commonly near Greyed-Purple Group 183C blended with near Yellow-Green Group 146A with venation of between Greyed-Purple Group 183C and 183D.

*Old foliage*.—Upper surface color: commonly near Green Group 137A with venation of near Green Group 137B. — under surface color: commonly near Green Group 137C with venation of near Green Group 137D.

*Petiole*.—Upper surface: color is commonly near Green Group 143A and texture is smooth. — under surface: color is commonly near Green Group 143B and texture is glandular. — length: approximately 6.0 cm on average. — diameter: approximately 1.0 mm on average.

*Rachis*.—Color of upper surface: commonly near Green Group 143A. — color of under surface: commonly near Yellow-Green Group 144B. — length: approximately 6.0 mm on average. — diameter: approximately 1.0 mm on average.

*Stipules*.—Margin: entire to erose. — length: approximately 1.5 cm on average. — width: approximately 5.0 mm on average. — color of upper surface: commonly near Green Group 143A. — color of lower surface: commonly near Green Group 143B.

*5-leaflet leaf*.—Length: approximately 11.0 cm on average. — width: approximately 10.5 cm on average.

*Leaf margin*.—Serrate.

*Leaf undulation*.—Weak.

Leaflets:

*Number of leaflets*.—3, 5, and 7.

*Shape*.—Ovate; apex is rounded to moderately acute; and base is rounded.

*Texture*.—Upper and under surfaces is smooth.

*Terminal leaflet*.—Length: approximately 6.0 cm on average. — width: approximately 4.0 cm on average.

*Lower leaflet*.—Length: approximately 4.2 cm on average. — width: approximately 2.5 cm on average.

Inflorescence:

*Number of flowers*.—Generally about 20 blooms on average on a plant at once.

*Number of blooms per stem or in a cluster*.—Occasionally 1 bloom per stem, more commonly up to 5 blossoms in a cluster per stem.

*Peduncle*.—Length: approximately 3.0 cm on average. — diameter: approximately 4.0 mm on average. — surface texture: smooth to moderately glandular. — color: commonly near Yellow-Green Group 144B.

*Sepals*.—Number: commonly 5. — length: approximately 2.5 cm on average. — width: approximately 1.0 cm on average. — margin: entire with extensions on two or three sepals measuring approximately 5.0 mm in length on average and 1.0 mm in width on average. — upper surface color and texture: commonly near Yellow-Green Group 144A; covered in short pubescence. — under surface color and texture: commonly near Yellow-Green Group 144B; puberulent. — apex: acute to aristate. — base: truncate as it joins the receptacle.

*Bud*.—Shape: ovoid. — length: approximately 2.0 cm on average. — width: approximately 2.0 cm on average. — color when opening: commonly near Red Group 51B.

*Flower*.—Diameter: approximately 9.0 cm on average. — height: approximately 4.5 cm on average. — duration: flower is on the plant approximately 5-7 days. — shape: cuplike. — form: double. — profile: very cup-like upon opening and when fully open profile becomes more convex. — number of petals under normal conditions: approximately 30 petals on average. — shape of the petal: overall: broadly obovate. apex: rounded. base: cuneate. — petal length: approximately 4.0 cm on average. — petal width: approximately 3.5 cm on average. — petal margin: entire and moderately undulating. — petal drop: excellent. — petaloids: commonly 3 to 5 present; color of upper and under surfaces is commonly near Red Group 54C with a very small basal spot of near Yellow-Orange Group 19B; length is approximately 2.0 on average; and width is approximately 1.0 cm on average. — fragrance: moderately strong sweet scent. — petal color when first and fully open: — upper surface: commonly near Red Group 54C with a very small basal spot of near Yellow-Orange Group 19B. — under surface: commonly near Red Group 54D with a very small basal spot of near Yellow-Orange Group 19C. — petal color at end of blooming: — upper surface: commonly near Red Group 55C with a basal spot of near Yellow-Orange Group 18D. — under surface: commonly near Red Group 55C with no basal spot.

*Receptacle*.—Color: commonly near Yellow-Green Group 144A. — diameter: approximately 1.0 cm on average. — depth: approximately 1.0 cm on average. — surface texture: smooth. — shape: Urn-shaped.

*Stamen*.—Number is approximately 67 on average. — anthers: number is approximately 67 on average; color is commonly near Yellow-Orange Group 15A; length is approximately 2.0 mm on average; and shape is oval. — filaments: length is approximately 9.0 mm on average and color is commonly near Yellow Group 3A.

*Pistils*.—Arrangement is separate and free; number is approximately 95 on average. — styles: length is approximately 3.0 mm on average and color is commonly near Orange Group 27B. — stigmas: diameter is typically less than 1.0 mm and color is commonly near Yellow Group 11A.

*Pollen*.—Color is commonly near Yellow Group 13B and a sparse amount is present.

*Hips*.—None observed.

Development:

*Vegetation*.—Semi-glossy, dark green, vigorous and strong.

*Blooming*.—Abundant and substantially continuous from spring through frost; which is typically May to November in Southeastern Pennsylvania.

*Resistance to disease*.—Very good resistance for black spot (*Diplocarpon rosae*).

*Hardiness*.—Hardy to USDA Zone 4.

The new 'Radbeauty' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of rose plant characterized by the following combination of characteristics:

(a) forms attractive, cup-like shaped, pink colored blossoms, (b) displays a very bushy and rounded growth habit, (c) forms vigorous vegetation, and (d) provides attractive ornamental dark green, semi-glossy foliage;

substantially as herein shown and described.

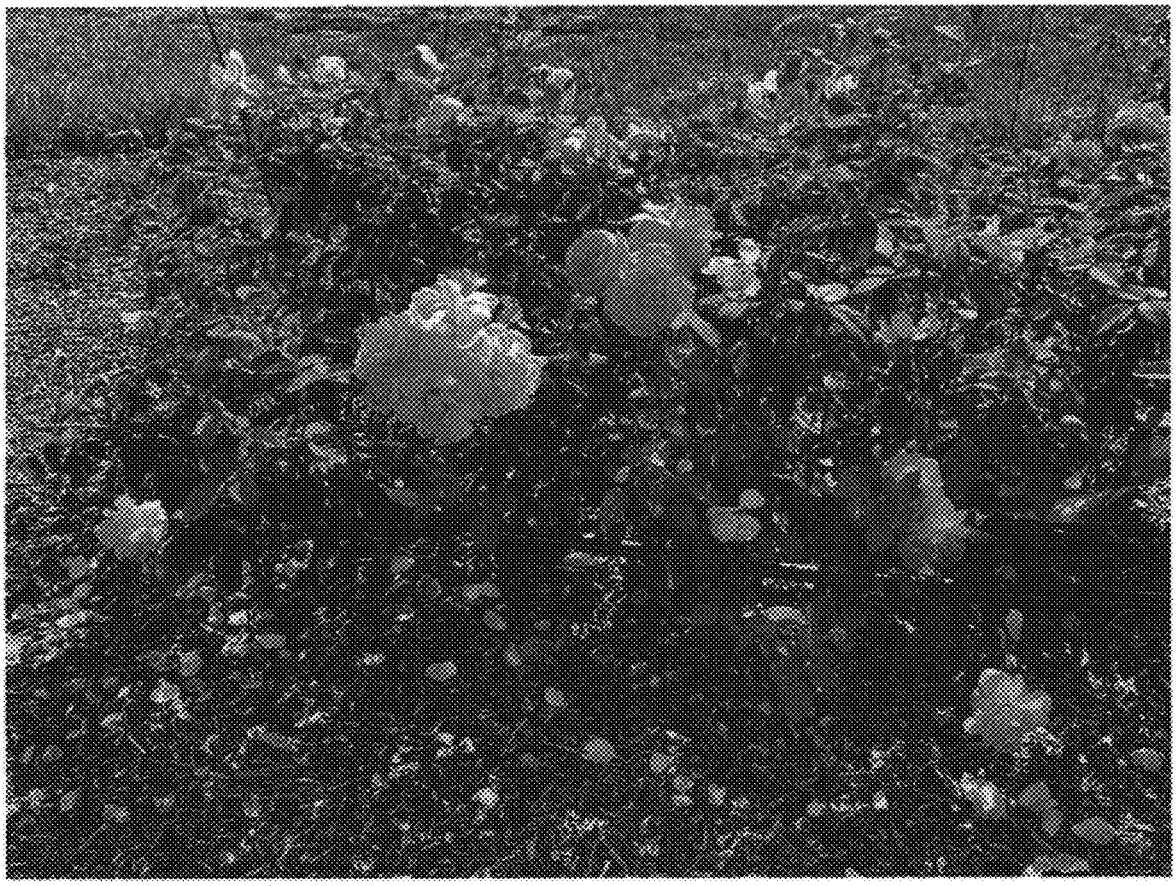

* * * * *